United States Patent [19]

Choi

[11] 3,945,897
[45] Mar. 23, 1976

[54] PHOTOHALOGENATION OF LACTAMS AND CERTAIN PRODUCTS THEREOF

[75] Inventor: Sam Kwon Choi, Seoul, South Korea

[73] Assignee: Chevron Research Company, San Francisco, Calif.

[22] Filed: Nov. 8, 1974

[21] Appl. No.: 522,036

Related U.S. Application Data

[62] Division of Ser. No. 309,082, Nov. 24, 1972, Pat. No. 3,875,147.

[52] U.S. Cl.............. 204/158 HA; 260/239.3 R; 260/239 A; 260/326.5 FL; 260/78 L; 260/78 P; 252/431 N; 252/475; 252/476; 252/443; 252/426; 252/441; 252/442
[51] Int. Cl.² .............C07D 205/06; C07D 207/26; C07D 223/10
[58] Field of Search 260/239 A, 239.3 R, 326.5 FL; 204/158 HA

[56] References Cited
UNITED STATES PATENTS 2,311,507  2/1943  Arthur .......................... 260/239.3 R
3,045,009  7/1962  Rogers ......................... 260/239.3 R Primary Examiner—John D. Randolph
Assistant Examiner—Robert T. Bond

[57] ABSTRACT

As new compositions of matter, a halogenated lactam of the formula:

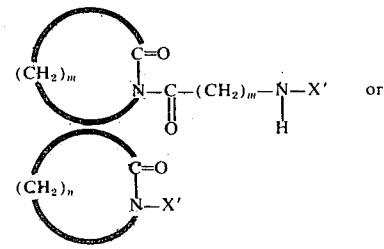

and a complex of a Lewis acid of the formula $MX_a$ and said halogenated lactam, wherein $m$ is 2 or 3;
$n$ is 5 to 11;
M is a metal of Group IIIA, IVA, VA, VIA, or IVB of the Periodic Table;
$a$ is the valence of M; and
X and X' are independently chlorine or bromine.

The Lewis acid-halogenated lactam complex is used as a polymerization activator in the polymerization of 2-pyrrolidone.

The halogenated lactam is formed by halogenating the desired lactam, and the Lewis acid-halogenated lactam complex is formed by reacting the desired halogenated lactam with said Lewis acid of the formula $MX_a$.

8 Claims, No Drawings

PHOTOHALOGENATION OF LACTAMS AND CERTAIN PRODUCTS THEREOF

This is a division of application Ser. No. 309,082, filed Nov. 24, 1972, now U.S. Pat. No. 3,875,147, issued Apr. 1, 1975.

DESCRIPTION OF THE INVENTION

This invention relates to a novel complex and a novel halogenated lactam, methods for their preparation, and methods for the polymerization of 2-pyrrolidone employing said complex and/or said halogenated lactam.

Methods for the polymerization of 2-pyrrolidone to form polypyrrolidone have been extensively disclosed in the literature, from as early as U.S. Pat. Nos. 2,638,463, 2,809,958 and 2,891,038, to as recent as British Patent No. 1267,446. In general, 2-pyrrolidone is polymerized in the presence of an alkaline polymerization catalyst, usually with an activator or co-catalyst.

The polymer formed from 2-pyrrolidone is believed to be a linear polyamide, which has come to be known as nylon-4, having the structure:

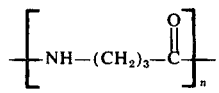

The polymer may be shaped into ribbons, films, molded articles and fibers.

The present invention provides a method of making a polymer of 2-pyrrolidone in solid form, which comprises polymerizing 2-pyrrolidone in the presence of an alkaline polymerization catalyst and, as an activator or co-catalyst, a complex of a Lewis acid and a halogenated lactam, which complex is postulated to have the general formula:

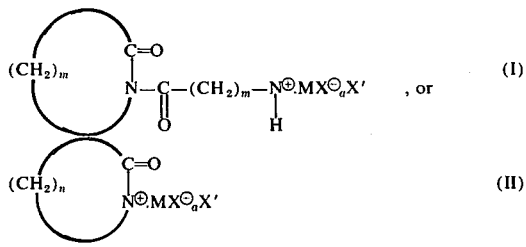

where $m=2$ or 3; $n=5$ to 11; M is a metal of Group IIIA, IVA, VA, VIA, or IVB of the Periodic Table; $a$ is the valence of M; and X and X' are independently chlorine or bromine.

In accordance with the method for the polymerization of 2-pyrrolidone to form polymers of 2-pyrrolidone in solid form, the Lewis acid-halogenated lactam complex (I) or (II) is either first formed outside of the polymerization mixture and is then added thereto, or the complex (I) or (II) is formed in situ by adding to a mixture of 2-pyrrolidone and an alkaline polymerization catalyst, a halogenated lactam of the formula:

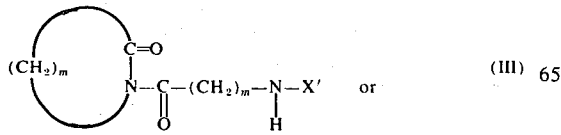

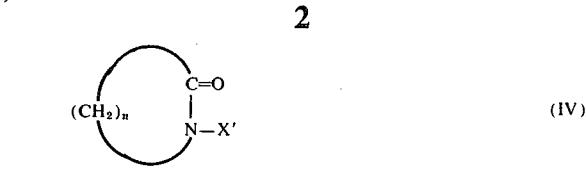

where $m$, $n$ and X' are as defined above,
and a Lewis acid of the formula:

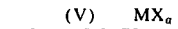

where M, X and $a$ are as defined above.

The present invention further provides, as novel chemical compounds, the halogenated lactam of the formula (III) or (IV) and the Lewis acid complex thereof of the formula (I) or (II).

DESCRIPTION OF THE PRIOR ART

It is known, of course, that trihalides of aluminum, bismuth and antimony, tetrahalides of tin, titanium, zirconium and lead and the pentahalide of antimony, have previously been proposed for use as activators in the polymerization of 2-pyrrolidone in U.S. Pat. No. 3,383,367 to Black and Morehead. Further, U.S. Pat. No. 3,405,099 to Taber proposes the use of tetrahalides of an element of Group IV, including the metals and non-metals. Both Black et al. and Taber proposed that their respective metal halides be added as polymerization activators to a mixture of 2-pyrrolidone monomer and an alkaline polymerization catalyst. Neither Black et al. nor Taber employed any halogenated lactam or Lewis acid complex.

When the halogenated lactam (III) or (IV) is used as an activator or co-catalyst, together with an alkaline polymerization catalyst, in the polymerization of 2-pyrrolidone, the resulting polymer is of extremely low molecular weight. Indeed, the results obtained using no activator at all, and only the alkaline polymerization catalyst, are not much different than using the combination of halogenated lactam (III) or (IV) and alkaline polymerization catalyst. However, while the halogenated lactam (III) or (IV) has almost no activity as an activator for the polymerization of 2-pyrrolidone, the Lewis acid-halogenated lactam complex (I) or (II) possesses very strong activity.

When the Lewis acid-halogenated lactam complex (I) or (II) is compared to the Lewis acid alone as an activator for the polymerization of 2-pyrrolidone, it is surprisingly found that the Lewis acid complex (I) or (II) of the invention is far more active than the Lewis acid, and, in addition, gives rise to a polymer of higher molecular weight. It is indeed surprising that the activity of the Lewis acid as a polymerization activator can be markedly increased by forming a complex of the Lewis acid (V) and the halogenated lactam (III) or (IV), since the halogenated lactam (III) or (IV) has substantially no activity as a polymerization activator.

PREPARATION OF HALOGENATED LACTAM

The new halogenated lactams (III) or (IV) of the present invention may be conveniently formed by chlorinating or brominating the desired lactam of the formula:

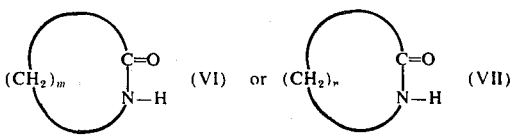

where *m* and *n* are as defined above, such as by the use of chlorine gas or liquid bromine in the presence of ultraviolet light.

Thus, the desired lactam may be dissolved in any suitable inert organic solvent that is customarily used for halogenation reactions, such as carbon tetrachloride, and the chlorine gas or liquid bromine is introduced into the solution of the lactam while the solution is being irradiated with ultraviolet light. The reaction between gaseous chlorine and 2-pyrrolidone in the presence of ultraviolet light takes place within two or three minutes, as evidenced by the formation of a solid reaction product, which precipitates out of the solution. With other lactams, the halogenation reaction has a longer induction period, and generally the bromination reaction is slower than the chlorination reaction. Both the chlorination and bromination of the desired lactam are satisfactorily carried out at room temperature and atmospheric pressure, but, if desired, higher or lower temperatures can be employed, bearing in mind the melting and boiling points of the solvent. That is, the lower limit for the halogenation reaction will be determined by the desire to maintain a liquid phase, and the upper limit will be determined in large measure by the desire to maintain the solvent in solution rather than boiling it off by the use of excessively high temperatures. A satisfactory temperature range for the halogenation reaction is 20°C to 40°C and any convenient pressure may be used ranging from subatmospheric to superatmospheric. The halogenation reaction time is not critical, and generally the halogenation reaction will be completed in from about 15 minutes to 1 hour. With the higher lactams, longer reaction times may be needed.

The halogenated lactam is in the nature of a dimer when it is formed from the lower lactams, azetidinone and 2-pyrrolidone, whereas the halogenated lactam has the halogen directly attached to the ring nitrogen atom when it is formed from the higher lactams, namely caprolactam ($n = 5$) through ω-lauroyllactam ($n = 11$). Those lactams where $m = 2$ or 3, namely azetidinone and 2-pyrrolidone, and those where $n = 5$–8, namely caprolactam, enantholactam, caprylolactam and ω-nonanoyllactam, are preferred lactams for use in forming the halogenated lactam (III) or (IV), and hence the halogenated lactam complex (I) or (II), since these lactams are more readily available and less expensive than the lactams with more carbon atoms.

PREPARATION OF LEWIS ACID COMPLEX

The Lewis acid-halogenated lactam complex (I) or (II) is readily formed by contacting the desired Lewis acid (V) with the halogenated lactam (III) or (IV). The reaction between the Lewis acid (V) and the halogenated lactam (III) or (IV) is very exothermic and a solid reaction product is rapidly formed that contains the desired Lewis acid-halogenated lactam complex (I) or (II). Thus, no special reaction conditions are necessary to form the Lewis acid-halogenated lactam complex (I) or (II), since room temperature and ordinary pressure are quite suitable. Likewise, either the Lewis acid (V) or the halogenated lactam (III) or (IV) may be present in excess of equimolar proportions.

The Lewis acid moiety of the complex (I) or (II), is a chloride or bromide of a metal of Groups IIIA through VIA and IVB of the Periodic Table, namely aluminum, gallium, indium, tantalum, germanium, tin, lead, antimony, bismuth, polonium, titanium, zirconium and hafnium. Such metal halides are known as Friedel-Crafts catalysts. It is presently preferred to use aluminum chloride or stannic chloride as the Lewis acid to form the Lewis acid-halogenated lactam complex (I) or (II) of the present invention, due to their ready availability and relative ease of handling as compared to other Lewis acids.

It is presently believed that the complex (I) or (II) has the formula (I) or (II) set forth above, but the precise structural formula therefor has not yet been completely determined. For convenience, the present application refers to the "complex (I) or (II)" as meaning the complex formed by reacting the Lewis acid (V) with the halogenated lactam (III) or (IV).

POLYMERIZATION OF 2-PYRROLIDONE

The reaction conditions for the polymerization of 2-pyrrolidone in accordance with the present invention are essentially the same as that known in the prior art.

Thus, the polymerization may be carried out at a temperature from about 18°C to about 100°C, and preferably from about 25°C to about 70°C. The pressure during the polymerization may range from superatmospheric pressure to subatmospheric pressure, and atmospheric pressure is preferred. Bulk polymerization or suspension polymerization may be used. The technique described in U.S. Pat. No. 2,739,959 is also suitable.

The alkaline polymerization catalyst may be any of those used in the art for the polymerization of 2-pyrrolidone, such as those disclosed in previously mentioned U.S. Pat. No. 2,638,463. Alkali metals, or any other agent that may reduce the sensitive 2-pyrrolidone ring and thereby introduce impurities into the polymerization, are avoided.

Suitable catalysts are derivatives of the alkali metals, e.g. the hydrides, hydroxides and oxides of the alkali metals. The alcoholates of the alkali metals, such as sodium methylate, may also be used with good results. The preferred catalyst is the alkali metal salt of 2-pyrrolidone, e.g. sodium or potassium pyrrolidonate.

In addition, the oxides and hydroxides of the alkaline earth metals, for example, calcium and barium, may be used as catalysts. Also, organic metallic compounds, preferably those which are strongly basic, may be used, such as the lithium, potassium and sodium alkyls, e.g. butyl lithium, and the aryls of the alkali metals, such as sodium phenyl and sodium amide. The catalyst may be a quaternary ammonium base as described in U.S. Pat. No. 2,973,343 of the formula:

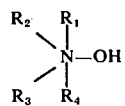

wherein $R_1$, $R_2$ and $R_3$ are lower alkyl radicals and $R_4$ is an alkyl, aryl or aralkyl radical. Further, as previously mentioned, the catalyst may be an alkali metal hydride, such as sodium hydride, as described in U.S. Pat. No. 3,075,953. While certain alkali metal derivatives can be used, many of them are undesirable. For example, the alkali metal carbonates as well as the alkaline earth metal hydroxides tend to be insoluble and for this reason are undesirable. Lithium hydroxide (monohydrate) also is insoluble in 2-pyrrolidone.

The catalyst may be used in an amount of 0.5 to 50% by weight, based on the 2-pyrrolidone monomer, preferably 5 to 30 wt. percent, most preferably 8 to 20 wt. percent.

It is desirable to carry out the polymerization in the substantial absence of water, although anhydrous conditions are not essential; e.g. the amount of water should not exceed about 0.1% by weight of the 2-pyrrolidone monomer.

A preferred technique is to heat under vacuum to 120°C or below a mixture of 10 mols of 2-pyrrolidone and 1 mol of KOH while removing water formed during the reaction to provide an anhydrous solution of potassium pyrrolidonate in 2-pyrrolidone and to add the Lewis acid-halogenated complex (I) or (II) to this solution.

The Lewis acid-halogenated lactam complex (I) or (II), which is used as the activator or co-catalyst, is used in an amount of from trace quantities up to about 80 mol percent, preferably up to about 30 mol percent, based on the mols of the alkaline polymerization catalyst. For purposes of calculation, it is assumed that the complex has the structural formula (I) or (II) set forth above. Generally, good results are obtained using from about 0.1 to about 20 mol percent of the complex, but even a trace amount of the complex exerts a strong activating and/or co-catalytic effect.

The Lewis acid-halogenated lactam complex (I) or (II) is quite hygroscopic, and for this reason it is desired to form the Lewis acid-halogenated lactam complex (I) or (II) in situ for use in the polymerization of 2-pyrrolidone. As is well known, the polymerization of 2-pyrrolidone is preferably carried out under substantially anhydrous conditions and the addition of a hygroscopic material that carried with it substantial quantities of bound water would not be desirable. Nevertheless, the addition of the pre-formed Lewis acid-halogenated lactam complex (I) or (II) to a mixture of 2-pyrrolidone monomer and alkaline polymerization catalyst does indeed result in a polymerization to form a solid polymer of 2-pyrrolidone.

It is preferred, therefore, to carry out the polymerization of 2-pyrrolidone in the presence of the Lewis acid-halogenated lactam complex (I) or (II) by the formation of such complex in situ through the addition to a substantially anhydrous mixture of 2-pyrrolidone and alkaline polymerization catalyst of the halogenated lactam (III) or (IV) and the desired Lewis acid (V).

The present invention is illustrated by the following Examples.

As used herein, inherent viscosity is defined as equal to:

$$\frac{2.303}{C} \log \frac{t_s}{t_o}$$

where
- $C$ = concentration of polymer in solvent in grams per deciliter
- $t_s$ = flow time of solution
- $t_o$ = flow time of pure solvent Inherent viscosity is reported herein in terms of a 0.5 g/dl solution of polymer in anhydrous hexafluoroisopropanol at 25°C, unless otherwise stated.

The maximum initial rate of decomposition and the time to 90% decomposition reported in the Examples were determined using a DuPont Thermogravimetric Analyzer, Model 950, operated isothermally at 300°C. The maximum initial rate of decomposition is determined by calculating the steepest slope of the curve of percent decomposition versus time.

EXAMPLE 1

Preparation of Chlorinated Pyrrolidone

A solution of 50 grams of 2-pyrrolidone in 100 ml of carbon tetrachloride was placed in a quartz tube and the solution irradiated at room temperature with short wave ultraviolet light for 15–20 minutes while chlorine gas was bubbled through. A white precipitate formed after 2 to 3 minutes, and the precipitate stopped forming after about 15–20 minutes. After termination of the chlorination, the crude solid product obtained was filtered off and washed three times with 100 ml portions of benzene. The crude product was then recrystallized from acetone and 63 grams (90 percent of the theoretical yield) of final product was obtained, having a melting point of 88°–89°C. Analysis of the final product determined that it had the following structural formula:

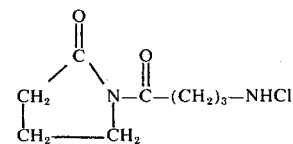

Analysis: I.R. C = O band at 1670 cm$^{-1}$: NH (singlet) band at 3320 cm$^{-1}$: Calculated for $C_8H_{13}N_2O_2Cl$: C, 47.05; H, 6.37; N, 13.72; Cl, 17.16. Found: C, 46.83; H, 7.05; N, 13.55; Cl, 17.00.

EXAMPLE 2

Preparation of Chlorinated Caprolactam

Following the procedure of Example 1, a solution of 10 grams of caprolactam in 100 ml of carbon tetrachloride was placed in a quartz tube and irradiated at room temperature with short wave ultraviolet light while chlorine was bubbled through for 20–30 minutes. A solid product formed shortly after the chlorine gas was introduced into the solution and settled to the bottom of the tube. At the end of the chlorination reaction, the solid product was filtered off and washed several times with 100 ml portions of benzene. The product was recrystallized from acetone and 2.8 grams (43 percent of theory) of final product was obtained having a melting point of 152°–153°C. Infrared and other analysis established the structure of the final product as:

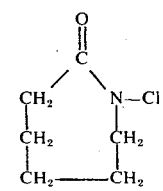

Analysis I.R. NH band at 3220 cm$^{-1}$ disappeared: C=O band at 1640 cm$^{-1}$: Calculated for $C_6H_{10}NOCl$: C, 48.97; H, 6.8; N, 9.25; Cl, 23.7. Found: C, 48.87; H, 7.98; N, 9.25; Cl, 22.85.

EXAMPLE 3

Polymerization of 2-Pyrrolidone Using Lewis Acid-Halogenated Pyrrolidone as Initiator A mixture of 42.5 grams (0.5 mol) of 2-pyrrolidone and 4.25 grams of KOH pellets (85% by weight assay) was heated at a temperature of about 103°C for 2 minutes under 4 mm Hg pressure to remove the water formed. The resulting anhydrous solution was cooled to room temperature and 2 grams of the chlorinated pyrrolidone obtained from Example 1 were added to the solution and completely dissolved therein. A trace amount (about 2–3 mg) of $AlCl_3$ was added and the system flushed with nitrogen gas. The polymerizate was poured into a polyethylene bottle and held at a temperature of 45°–50°C for 20 hours. At the end of this period of time, the solid polymer thus formed was removed from the bottle, and washed with water to remove unreacted monomer and KOH. The percent conversion of monomer to polymer was 43 percent, by weight, and the polymer had an inherent viscosity of 4.00 dl/g.

Following this procedure, additional runs were made using larger amounts of aluminum chloride and employing different reaction times and polymerization temperatures. In addition, three runs were carried out in which no chlorinated pyrrolidone was employed. The results of all of these runs are reported in Table I below.

TABLE I

| | Amount of Chlorinated Pyrrolidone | Amount of | Polymerization Data | | | |
|---|---|---|---|---|---|---|
| Run | (g) | $AlCl_3$ (g) | Time (hr.) | Temp. (C°) | % Conv. | I.V.* (dl/g) |
| 1 | 2 | trace | 20 | 45–50 | 43 | 4.00 |
| 2 | 2 | trace | 40 | 45–50 | 51 | >4.61 |
| 3 | 2 | trace | 24 | 25 | 41 | 3.72 |
| 4 | 3 | 1.5 | 50 | 45–50 | 51 | 4.61 |
| 5 | 3 | 1.0 | 70 | 45–50 | 59 | >4.61 |
| 6 | none | 1.19 | 25 | 25 | 18 | <2.7 |
| 7 | none | 1.19 | 50 | 25–50 | 35 | 3.41 |
| 8 | none | 1.19 | 25 | 45–50 | 26 | 3.00 |

*I.V. = Inherent viscosity

A comparison of Runs 1–5 with any of Runs 6, 7 and 8 immediately shows the advantages of the present invention over the use of a Lewis acid alone as the initiator. Thus, in Runs 6, 7 and 8, the Lewis acid, $AlCl_3$, was used as the activator, as compared with Runs 1–5 where the Lewis acid-chlorinated pyrrolidone complex was used. In every case, the polymer of Runs 1–5 had a substantially higher inherent viscosity, and therefore a substantially higher molecular weight, than the polymer of Runs 6–8. The use of even a trace amount of aluminum chloride with the chlorinated pyrrolidone to form a trace amount of the complex, as in Runs 1, 2 and 3, results in a substantially higher molecular weight than can be obtained even with the large amounts of aluminum chloride used in Runs 6, 7 and 8. Furthermore, a comparison of Run 1 with Run 8 shows that the use of the aluminum chloride alone gives rise to about half the conversion of monomer to polymer as the use of even a trace amount of the complex formed by in situ reaction of a trace amount of aluminum chloride with the chlorinated pyrrolidone.

EXAMPLE 4

Polymerization of 2-Pyrrolidone Using a Complex of Chlorinated Pyrrolidone and $SnCl_4$ as Activator Following the procedure of Example 3, 2-pyrrolidone was polymerized using as the activator stannic chloride alone or the stannic chloride-chlorinated pyrrolidone complex. The amounts of 2-pyrrolidone monomer and KOH and the manipulative techniques are as in Example 3. The amount of $SnCl_4$ and chlorinated pyrrolidone, and the results of the polymerization, are reported in Table II below.

TABLE II

| | Amount of Chlorinated Pyrrolidone | Amount of | Time | Polymerization Data | | I.V.* |
|---|---|---|---|---|---|---|
| Run | (g) | $SnCl_4$(g) | (hr.) | Temp. (C°) | % Conv. | (dl/g) |
| 1 | none | 1.5 | 25 | 45–50 | 19 | 3.00 |
| 2 | none | 1.5 | 50 | 45–50 | 31 | 3.29 |
| 3 | none | 1.5 | 70 | 45–50 | 39 | 3.5 |
| 4 | 2.6 | 1.5 | 20 | 25 | 38 | 4.30 |
| 5 | 2.6 | 1.5 | 20 | 45–50 | 41 | >4.61 |
| 6 | 2.6 | 1.5 | 40 | 45–50 | 48 | >4.61 |

*I.V. = Inherent viscosity

As in the case of Example 3, the use of the Lewis acid, stannic chloride, by itself, as in Runs 1, 2 and 3 of Example 4, results in the formation of a polymer having a significantly lower molecular weight than is obtained with the use of the stannic chloride-chlorinated pyrrolidone complex formed in situ in Runs 4–6. In addition, the use of the complex more than doubles the percent conversion for a given polymerization time, particularly in the early stages of the polymerization, as may be seen by comparing Run 1 with either of Runs 4 or 5.

EXAMPLE 5

Polymerization of 2-Pyrrolidone Using a Complex of Chlorinated Pyrrolidone and Various Lewis Acids as Activator Following the procedure of Example 3, 2-pyrrolidone was polymerized using various Lewis acids to form the Lewis acid-halogenated lactam complex. The amounts of 2-pyrrolidone monomer and KOH and the manipulative techniques are as in Example 3. Table III below reports the Lewis acid used, the amount of the Lewis acid used, the amount of chlorinated pyrrolidone, and the results of the polymerization. Included in Table III are TGA data on the polymers formed.

TABLE III

| Run | Lewis Acid | Amount of Lewis Acid (g) | Amount of Chlorinated Pyrrolidone (g) | Polymerization Data | | | | TGA Data | |
|---|---|---|---|---|---|---|---|---|---|
| | | | | Time (hr.) | Temp. (C°) | % Conv. | I.V.* (dl/g) | % dec./min. | Time to 90% Decomposition (min.) |
| 1 | $AlCl_3$ | trace | 2 | 25 | 50 | 48 | >4.61 | 17.0 | 12.1 |
| 2 | $SnCl_4$ | 1.5 | 2 | 25 | 25 | 43 | >4.61 | 19.5 | 10.3 |
| 3 | $SbCl_5$ | trace | 2 | 20 | 25 | 32 | >4.61 | 17.0 | 10.4 |
| 4 | $GeCl_4$ | 1.5 | 2 | 20 | 50 | 35 | 3.58 | 21.0 | 10.6 |
| 5 | $TiCl_4$ | trace | 2 | 20 | 25 | 43 | 4.61 | 23.5 | 8.2 |
| 6 | $ZrCl_4$ | 1.5 | 2 | 20 | 50 | 41 | 4.30 | 21.0 | 11.5 |

TABLE III-continued

| Run | Lewis Acid | Amount of Lewis Acid (g) | Amount of Chlorinated Pyrrolidone (g) | Polymerization Data | | | | TGA Data | |
|---|---|---|---|---|---|---|---|---|---|
| | | | | Time (hr.) | Temp. (C°) | % Conv. | I.V.* (dl/g) | % dec./min. | Time to 90% Decomposition (min.) |
| 7 | HfCl₄ | 1.5 | 2 | 20 | 50 | 40 | 4.30 | 22.0 | 10.7 |

*I.V. = Inherent viscosity

These data show the consistently high molecular weight nylon-4 obtained with a wide variety of Lewis acid-chlorinated pyrrolidone complexes and the thermal stability data, reflected by the percent decomposition per minute and the time to reach 90 percent decomposition, indicate that the resulting polymers are thermally stable.

EXAMPLE 6

Polymerization of 2-Pyrrolidone Using a Complex of Chlorinated Caprolactam and Various Lewis Acids as Activator The procedure of Example 3 was followed to polymerize 2-pyrrolidone using as the activator a Lewis acid-chlorinated caprolactam complex. In this Example, the amount of 2-pyrrolidone and KOH and the manipulative technique are as specified in Example 3. Instead of the 2 grams of chlorinated pyrrolidone employed in Example 3, 1.5 grams of chlorinated caprolactam obtained by the procedure of Example 2 were employed. Table IV below reports the specific Lewis acid used, the amount of the Lewis acid used and the results of the polymerization. Again, the thermal stability data show that the resulting polymers are thermally stable.

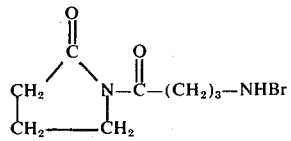

Analysis: I.R. C=O band at 1670 cm⁻¹: NH (singlet) band at 3120 cm⁻¹: Calculated for $C_8H_{13}N_2O_2Br$: C, 38.55; H, 5.22; N, 11.24; Br, 32.12. Found: C, 37.88; H, 5.75; N, 10.88; Br, 32.25.

EXAMPLE 8

Polymerization of 2-Pyrrolidone Using a Complex of Brominated Pyrrolidone and AlBr₃ as Activator A mixture of 42.5 g (0.5 mol) of 2-pyrrolidone and 4.25 g of potassium hydroxide pellets (85 percent assay) was heated at about 103°C for 2 minutes under 4 mm Hg pressure to remove the water formed. The resulting anhydrous solution was cooled to room temperature and 2.5 g of the brominated pyrrolidone of Example 7 was added with stirring until the brominated pyrrolidone was completely dissolved. A trace amount (2–3 mg) of AlBr₃ was added and the reaction system flushed with nitrogen gas. Polymerization was carried out at 50°C for 25 hours using the procedure of Example 3, and the resulting polymer was worked up as in Example 3. The percent conversion was 43 percent to a polymer having an inherent viscosity of >4.61 dl/g. The TGA analysis of the polymer showed it had a percent decomposition per minute of 17.3 and a time to 90 percent decomposition of 10.8 minutes.

TABLE IV

| Run | Lewis Acid | Amount of Lewis Acid (g) | Amount of Chlorinated Caprolactam (g) | Polymerization Data | | | | TGA Data | |
|---|---|---|---|---|---|---|---|---|---|
| | | | | Time (hr.) | Temp. (C°) | % Conv. | I.V.* (dl/g) | % dec./min. | Time to 90% Decomposition (min.) |
| 1 | AlCl₃ | trace | 1.5 | 25 | 50 | 45 | >4.61 | 18.5 | 10.7 |
| 2 | SnCl₄ | 1.5 | 1.5 | 25 | 25 | 41 | >4.61 | 20.0 | 10.6 |
| 3 | SbCl₅ | trace | 1.5 | 25 | 25 | 40 | >4.61 | 19.5 | 10.4 |
| 4 | GeCl₄ | 1.5 | 1.5 | 20 | 50 | 32 | 4.30 | 20.0 | 10.0 |
| 5 | TiCl₄ | trace | 1.5 | 20 | 25 | 45 | 3.84 | 24.5 | 8.9 |
| 6 | ZrCl₄ | 1.5 | 1.5 | 20 | 50 | 42 | 3.41 | 22.0 | 11.8 |
| 7 | HfCl₄ | 1.5 | 1.5 | 20 | 50 | 38 | 3.14 | 22.0 | 11.4 |

*I.V. = Inherent viscosity

EXAMPLE 7

Preparation of Brominated Pyrrolidone

A mixture of 11.3 g (0.125 mol) of 2-pyrrolidone and 20 g (0.125 mol) of bromine was dissolved in 200 ml of carbon tetrachloride, and the solution placed in a 250 ml three-necked flask. The reaction mixture was stirred by passing nitrogen gas into the solution at room temperature over a period of one hour, during which time the solution was irradiated with ultraviolet light. After termination of the reaction, the product thus obtained was filtered off and washed several times with 100 ml portions of benzene. The crude product was re-crystallized from acetone, giving 3.5 g (11 percent yield of theory) of final product having a melting point of 138°–138.5°C. Analysis of the final product showed it had the following structural formula:

EXAMPLE 9

Preparation and Isolation of Complex of Chlorinated Pyrrolidone and AlCl₃

A 2 g (0.01 mol) portion of chlorinated pyrrolidone of Example 1 was added to 50 ml of dry benzene (dried over LiAlH₄ overnight) in which 1.3 g (0.01 mol) of AlCl₃ was suspended, and a rise in temperature was immediately noted. The reaction mixture was stirred under a nitrogen atmosphere in an ice bath at 10°C for 30 minutes. When the stirring was terminated, the reaction product, consisting of the Lewis acid complex, settled to the bottom and was filtered off in a dry box. The solvent was removed from the final product in a vacuum oven overnight at room temperature. The final product was a solid which is believed to have the formula:

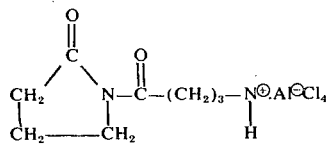

EXAMPLE 10

Polymerization of 2-Pyrrolidone Using Pre-formed Lewis Acid-Halogenated Lactam Complex as Activator A mixture of 42.5 g (0.5 mol) of 2-pyrrolidone and 4.25 g of potassium hydroxide pellets (85 percent assay) was heated at about 103°C for two minutes under 4 mm Hg pressure to remove the water formed. The resulting anhydrous solution was cooled to room temperature and then 3 g of the solid product of Example 9 was added and the system flushed with nitrogen gas. Polymerization was carried out at 50°C for 25 hours using the procedure of Example 3, and the resulting polymer was worked up as in Example 3. The conversion to polymer was 38 percent with the polymer having an inherent viscosity of >4.61 dl/g. The TGA analysis of the polymer showed that the polymer had a percent decomposition per minute of 19.3 and a time to 90 percent decomposition of 11.1 minutes.

I claim:

1. A method of making a compound of the formula:

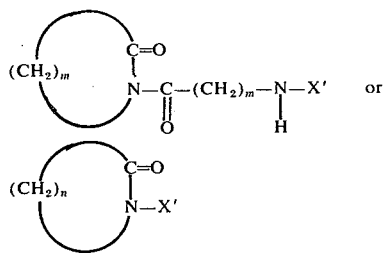 or which comprises contacting a solution of a lactam of the formula:

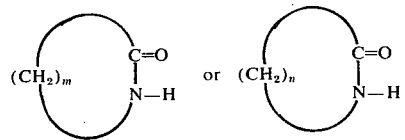

in an organic solvent with a hologenating agent selected from the group consisting of chlorine gas or liquid bromine in the presence of ultraviolet light, wherein $m$ is 2 or 3, $n$ is 5 to 11 and $X'$ is chlorine or bromine.

2. The method of claim 1, wherein said lactam is 2-pyrrolidone and the compound produced is:

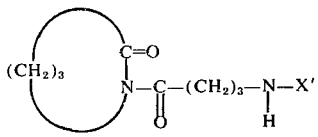

where $X'$ is chlorine or bromine.

3. The method according to claim 2, wherein the halogenating agent is chlorine gas and $X'$ is chlorine.

4. The method of claim 2, wherein the halogenating agent is liquid bromine and $X'$ is bromine.

5. The method of claim 1, wherein said lactam is caprolactam and the compound produced is:

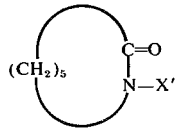

where $X'$ is chlorine or bromine.

6. A compound of the formula:

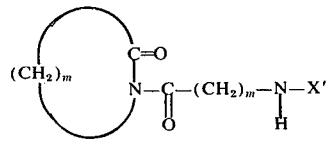

wherein
  $m$ is 2 or 3; and
  $X'$ is chlorine or bromine.

7. The compound of claim 6, wherein $m$ is 2 or 3.

8. The compound of claim 6, having the formula:

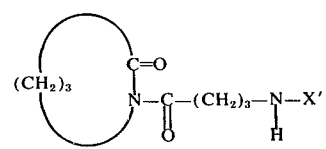

where $X'$ is chlorine or bromine.

* * * * *